US005826583A

United States Patent [19]

Wood

[11] Patent Number: 5,826,583

[45] Date of Patent: Oct. 27, 1998

[54] EMERGENCY SPINAL IMMOBILIZATION AND EXTRICATION DEVICE

[76] Inventor: Stephen P. Wood, 29 Normandy Rd., Lexington, Mass. 02173

[21] Appl. No.: 728,775

[22] Filed: Oct. 11, 1996

[51] Int. Cl.[6] .......... A61B 19/00

[52] U.S. Cl. .......... 128/869; 128/870; 5/627

[58] Field of Search .......... 128/845, 846, 128/869, 870, 876; 5/624, 626, 627, 628, 710, 913

[56] References Cited

U.S. PATENT DOCUMENTS

| | | | |
|---|---|---|---|
| 3,215,834 | 11/1965 | Tayman | 128/870 |
| 3,729,002 | 4/1973 | Miller | 5/627 |
| 4,301,791 | 11/1981 | Franco | 128/870 |
| 4,466,145 | 8/1984 | Jones | 5/627 |
| 4,885,811 | 12/1989 | Hayes | 128/870 |
| 5,121,756 | 6/1992 | Koledin | 128/870 |
| 5,154,185 | 10/1992 | Latimer | 128/870 |
| 5,626,150 | 5/1997 | Johnson | 128/870 |

*Primary Examiner*—Michael A. Brown
*Attorney, Agent, or Firm*—Mark P. White

[57] ABSTRACT

An emergency spinal immobilization and extrication device permits a victim of spinal column trauma to be firmly supported and immobilized for transportation to a health care facility. The device comprises a container filled with a multiplicity of small, resilient particles resting on a lightweight, rigid base-board, and having a sliding rigid cover. The container comprises means for inflating with gas and deflating. In operation the victim is placed on the cover and restrained at the ankles. As the cover is removed by sliding, the victim descends onto the container. The container is then deflated, leaving the victim supported by the particles which cling together as the gas is evacuated.

1 Claim, 3 Drawing Sheets

EMERGENCY SPINAL IMMOBILIZATION AND EXTRICATION DEVICE

BACKGROUND OF THE INVENTION

1. Field of the Invention

2. Description Relative to the Prior Art

The present invention relates to support and restraint systems used to immobilize a victim who has suffered injuries, particularly spinal injuries, prior to transportation of the victim to a hospital or clinic.

Victims suffering trauma, particularly trauma to the head, neck, and back, present special problems when transporting them from the site of the trauma to a treatment facility. Typical scenarios involve injuries from vehicle collisions, in which the victim must be first removed from the vehicle, placed in a horizontal position on a stretcher or the like, loaded into an ambulance, and driven to the final treatment facility. Under such circumstances, it is essential that the victim does not suffer additional injuries during the removal and transportation process arising out of further stress on the spinal cord.

Typical procedures under these scenarios involve restraining the victim on a stretcher by tying the victim with straps, and applying restraints alongside the neck and head in an attempt to immobilize the victim.

One presently known and used support of this type, introduced about during the Korean war, is the "spine board". The device is usually made from ¾" marine plywood and measures approximately 72" by 20". The victim is made fast to the board by means of three straps which are in turn secured to the board. The rigidity of the plywood tends to immobilize the victim. Marine plywood is used to resist deterioration with time, especially when the board is immersed in water, as during marine rescues and pool rescues after diving accidents.

To additionally support the victim, the region about the head and neck is often padded in a way to further immobilize the victim. Immobilization is especially important during transport of the victim to a care facility after the trauma. Towels are often used for padding, and these must be wadded up and carefully placed to avoid exacerbating the injuries further.

Shortcomings of the use of such restrain systems include the difficulty of placing the victim on the board without moving him in a way so as to minimize further injury. Furthermore, applying the padding must be done with the utmost of care, since the padding must be in intimate contact with the injured areas to give support to these areas, and yet they must be placed gently to avoid further injury.

A number of inventions have attempted to improve such restraint techniques. Common among these is the use of cushion, bags, and chambers which can be filled with a fluid to conform to the shape of a victim's body, or parts thereof. Air is particularly favored in this regard, due to its ubiquitous nature, and the low weight of an inflated container or compartment, at least in comparison to liquids such as water.

However, compartments filled with fluids do not conform easily to a victim's body, but rather tend to inflate in pre-determined shapes, regardless of the form within. However, recent inventions have used a multiplicity of small, solid particles, rather than fluids, to create a shape in conformance to a victim's body., Loeb et al. describes a vacuum mattress in which an envelope in filled with resilient particles, and is further fitted with means to evacuate the air from the envelope. When a victim is placed on this device, the mattress molds itself to the body of the victim. Removing the air causes the mattress to more or less "freeze" in the molded form. In the common implementations in which the mattress is filled with soft plastic particles, such as Styrofoam, the victim will then be embedded in a resilient matrix which will give him a high degree of support and prevent any major lateral movement.

Devices based on the Loeb patent have been used in the United States for transportation of spinal trauma victims, but have not gained widespread popularity because of a number of shortcomings of the invention.

First of all, the vacuum mattress by itself is not sufficiently rigid to properly support a trauma victim when lifted off the ground. Thus, the victim may be properly placed in the mattress while the mattress is lying on the ground or on a similar rigid surface, and the mattress evacuated to form the proper support. But when the evacuated mattress is lifted either by its ends or by its sides it tends to sag in the middle, thus subjecting the victim to further trauma in the vertical direction.

Secondly, for the vacuum mattress to work properly, the particles within must be more or less uniformly dispersed throughout the mattress before placing the victim on the mattress. However, after several uses the particles tend to bunch up or clump in specific areas of the mattress, and it becomes difficult to redistribute them properly. As a result, the mattress may not have sufficient material within to provide support for various parts of the victim's body.

Next, the vacuum mattress, even after evacuation, tends to lose its shape when the vehicle in which is situated is subjected to accelerations and deceleration in traffic.

Finally, the act of rolling or sliding the victim onto the unevacuated mattress often redistributes the particles within in an undesired way, resulting in insufficient support for the victim.

Other inventors have attempted to overcome these problems. U.S. Pat. No. 4,254,518 uses a vacuum mattress in conjunction with support elements formed by separated casings extending above the surface of the mattress to provide additional support. However, this invention does not deal with the problem of the redistribution of the particles caused by rolling or sliding the victim onto the mattress, or by acceleration of the vehicle used to transport the victim. Such redistribution represents a major problem in the prior art. The vacuum mattresses which are currently commercially available suffer from the redistribution problem, and it is thought that this redistribution is one of the major causes for the lack of commercial success of these vacuum mattresses.

The current invention deals with all of these problems. First of all, the rigidity problem is solved by combining the vacuum mattress with a rigid supporting surface beneath the mattress, so that the victim is not subjected to vertical stress once he is in placed on the mattress.

Next, the redistribution problem is solved by compartmentalizing the mattress into segments which roughly correspond to the human body, with particle density proportional to the relative average weight of the corresponding body portion. The segments are separated by partitions which do not allow the mattress particles to migrate across partitions, but do allow the gas which fills the mattress to freely move from one segment to the next.

Finally, placement of the victim on the mattress is facilitated by use of a slideable upper surface upon which the victim is initially placed, after which the upper surface is removed, allowing the victim to gently descend onto the surface of the vacuum mattress.

SUMMARY OF THE INVENTION

The limitations and disadvantages of the prior art discussed above are overcome by the present invention. It is an object of the present invention to provide a device for the immobilization and transportation of victims of spinal injury.

It is a further object of this invention to provide such a system which will minimize additional trauma whilst placing the victim on the device.

It is a still further object of this invention to provide such a device which will maintain its efficacy during accelerations and decellerations attendant to transportation by motor vehicle.

According to one aspect of the invention, an emergency spinal immobilization and extrication device comprises a gasproof flexible container filled with a plurality of deformable and resilient particles. The device further comprises means for inflating and deflating the container. And the device further comprises a rigid baseplate beneath the container so that the container will not collapse when the victim is placed on it.

According to another aspect of the invention the container further comprises a plurality of flexible sub-containers, wherein: each sub-container is filled with a plurality of deformable and resilient particles. Furthermore, each sub-container contains perforations permitting the gas to travel freely from any sub-container to another, but preventing the gas to exit the container. The perforations are sufficiently small so that the particles may not travel from any sub-container to another sub-container.

According to still another aspect of the invention, the sub-containers are arranged in a form approximately corresponding to the human body when lying upon the container in a supine position.

According to yet another aspect of the invention, the density of particles in the sub-containers are approximately proportional to the weight of that portion of the human body resting upon the container when the body is in a supine position.

According to still another aspect of the invention, the device comprises side pieces attached to the base plate, and a top cover is mounted to the side pieces such that the top cover may slide on and off the side pieces. Thus, the victim may be placed on the top cover in the "closed" position, and restrained by the ankles. When the cover is made to slide off, the victim is gradually and gently lowered onto the container.

DETAILED DESCRIPTION OF THE PREFERRED EMBODIMENTS

Before proceeding with a description of the preferred embodiments, the reader is advised to review the operation of the vacuum mattress by referring to Loeb, U.S. Pat. No. 4,045,830, which is incorporated herein by reference. The current invention constitutes substantial improvements over Loeb.

Figure 1:
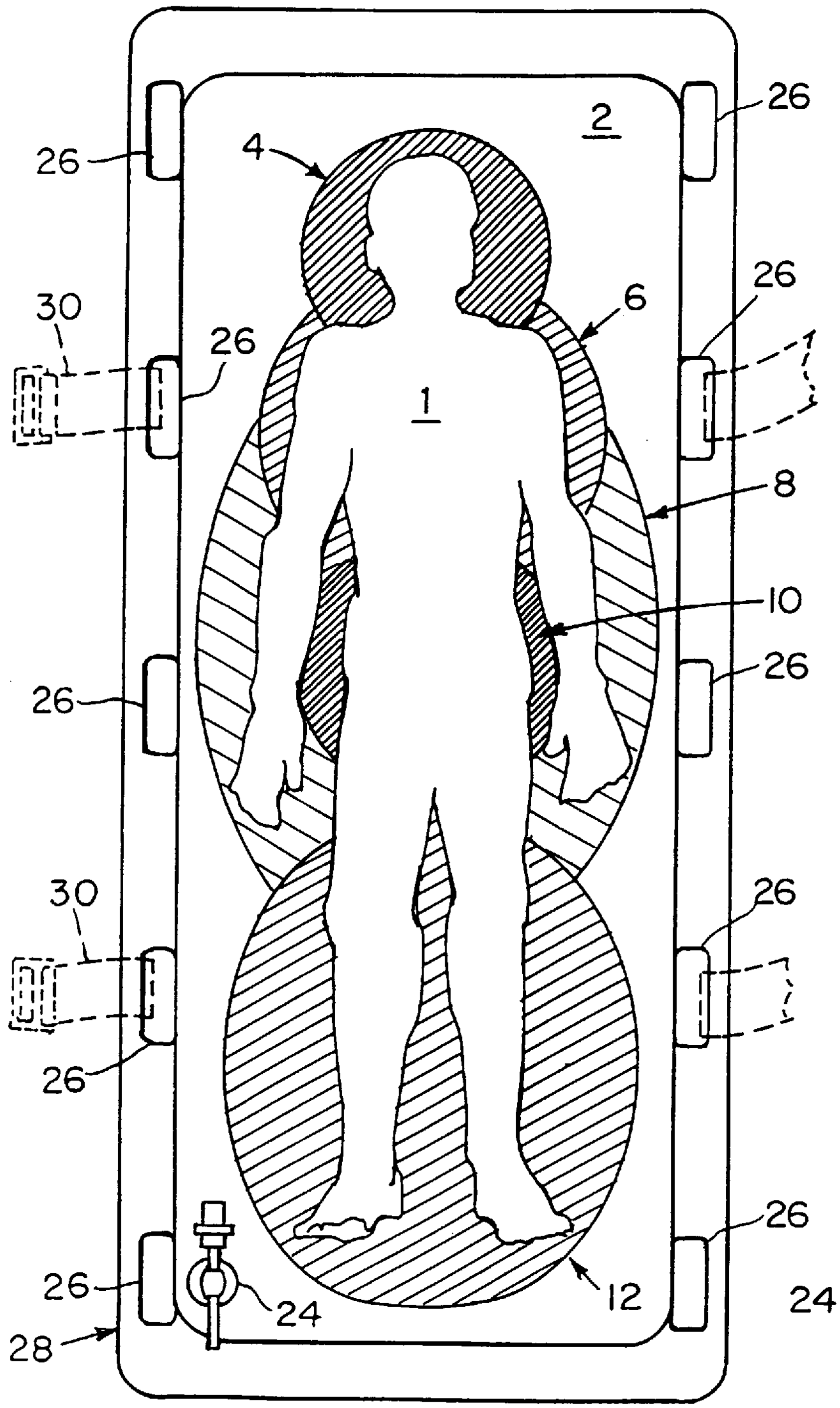
FIG. 1 depicts a top view of the first preferred embodiment.
Figure 2:
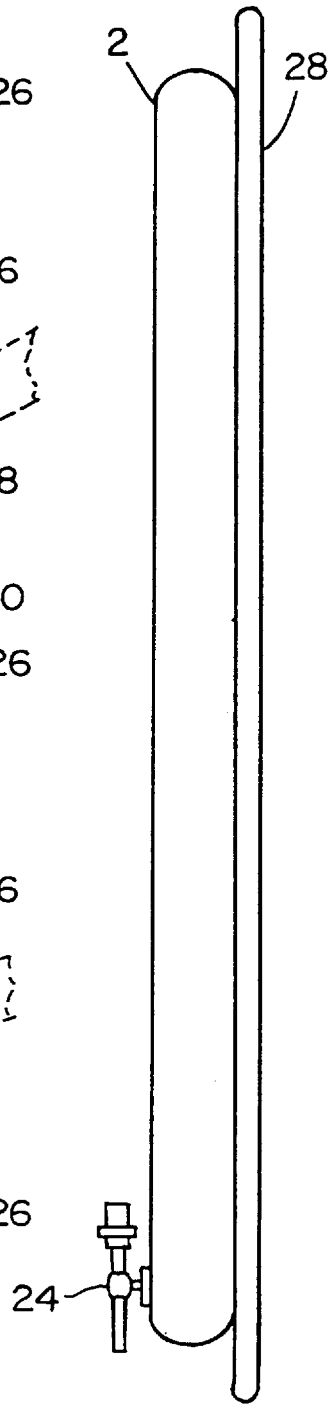
FIG. 2 depicts a side view of the first preferred embodiment.
Figure 3:
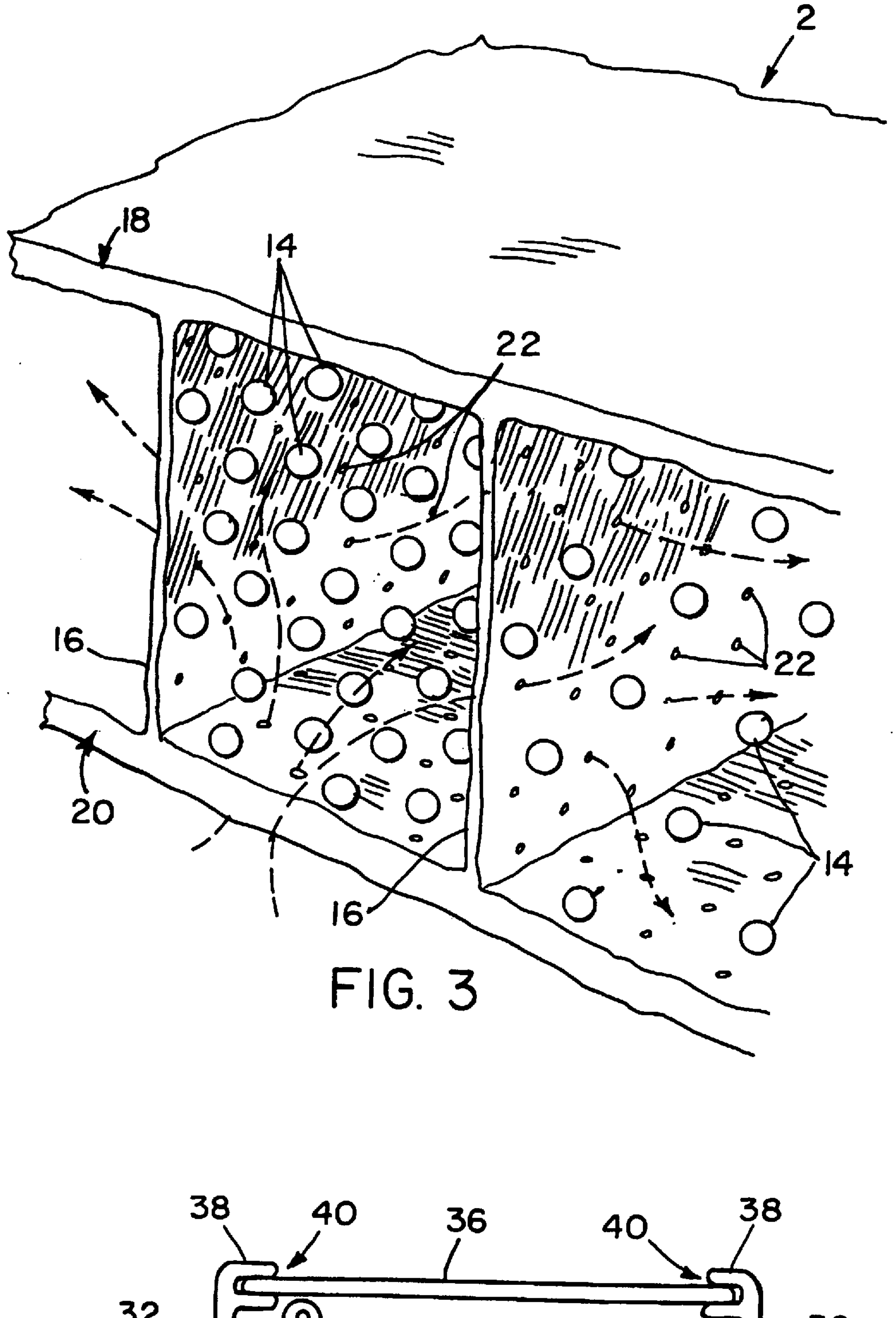
FIG. 3 depicts a cross section view of the vacuum mattress.

The first preferred embodiment of the present invention can be understood with reference to FIGS. 1, 2 and 3. FIG. 1 shows this embodiment as viewed from above. The victim 1 is shown lying on the vacuum mattress 2, which is composed of a number of distinct Mattress Body Regions (MBR), each of which roughly corresponds to a area of the human body: head region 4, shoulder region 6, mid-body region 8, buttock region 10, and leg region 12.

The vacuum mattress is filled with particles 14, which may be made of a number of substances, including plastics, rubber, or foam material, among others. The material should be strong and light, to provide support, but allow the device to be light enough to be easily handled by a single rescuer.

As seen in FIG. 1, each of the body regions is demarcated by a boundary which separates it from the other regions. These regions appear in FIG. 1 as cross hatched with different patterns. As seen by referring to FIG. 3, a boundary 16 extends from the top layer 18 of the vacuum mattress through the depth of the mattress, and ending at the bottom layer 20 of the mattress. The boundaries are further perforated by boundary holes, which are smaller than the particles 14 within the mattress, so that the particles may not migrate across the boundaries.

For the purpose of this discussion, it will be assumed that the particles within the vacuum mattress are of a more-or-less uniform size and weight, and the term "particle density" will be used to refer to the number of particles per cubic foot within a particular MBR.

It is a essential part of this embodiment that the particle density for each MBR vary with the approximate relative weight of the body region supported by the MBR. For example, suppose that the mid-body region 8 was found to support 10 percent of the body weight, and that the shoulder region 6 was found to support 30 percent of the body weight, based on a standard androgynous person. Then the particle density of the shoulder MBR should be about three times that of the mid-body MBR.

Because of the boundary between MBRs, the density of each MBR will not change with time, but will remain immutable, even after repeated fillings and evacuations of the mattress.

Because the particle density of each MBR will remain constant, and will be more or less proportional to the weight supported by that MBR, the victim will be supported in a more or less horizontal position on the mattress, receiving the needed extra support for the heavier part of the body.

When the victim is set in place on the mattress and arranged in the position as shown in FIG. 1, more or less, the gas which fills the mattress is evacuated by means of a valve 24. This valve may also be used to re-fill the mattress with gas when appropriate, since the mattress should be full prior to placing the victim on it.

The vacuum mattress rests on baseboard 28. This baseboard is made of a lightweight metal, plywood, or plastic. Its height and width must accommodate a wide range of human frames, and the preferred embodiment is approximately 76 inches by 24 inches. The baseboard contains a number of handholes 26, which also serve to as anchor points for the optional restraining straps 30.

Figure 6:
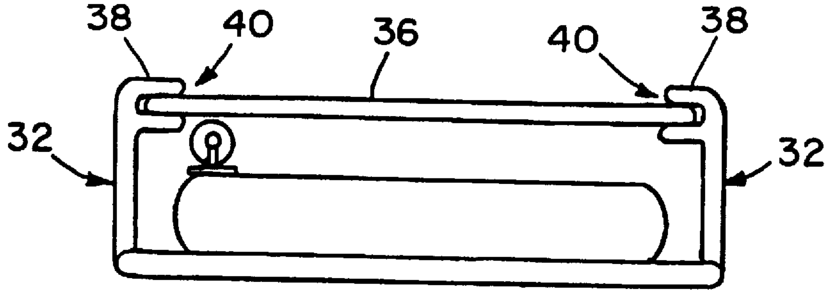
FIG. 6 depicts an end view of the second preferred embodiment.
Figure 4:
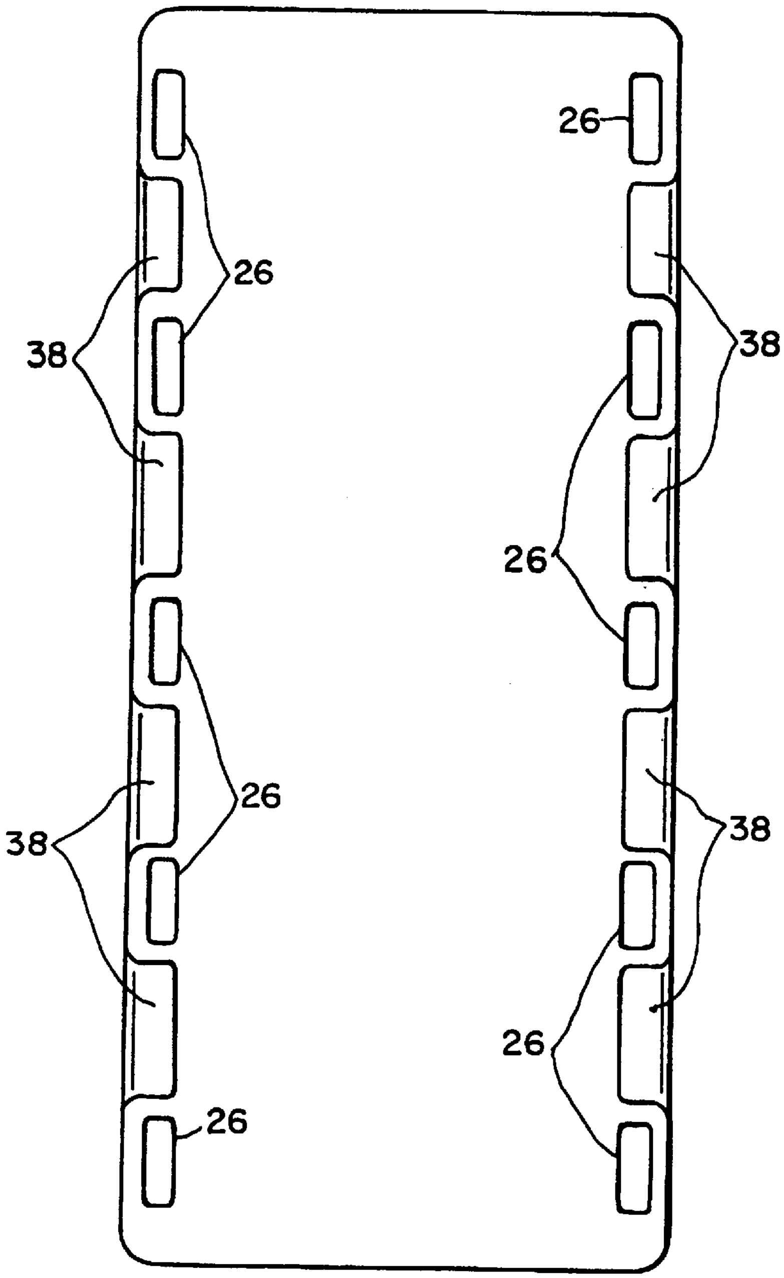
FIG. 4 depicts a top view of the second preferred embodiment.
Figure 5:
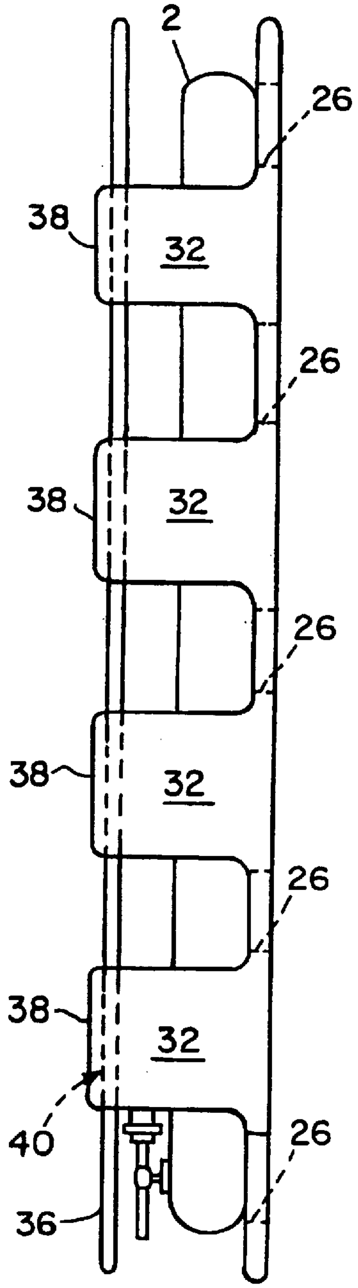
FIG. 5 depicts a side view of the second preferred embodiment.

A second embodiment may be understood with reference to FIGS. 4–6. This second embodiment contains all the elements of the first embodiment, but in addition comprises a top cover 36 which is slideably mounted in slides 40 which are attached to the upper edges of the side supports 32, which maintain the top cover above the mattress, as seen in FIGS. 5 and 6. The side supports in turn are formed into lands 38, which lend sufficient strength to the structure to support the top slide even when a person of several hundred pounds of weight is lying upon the cover. However, the space between the lands allows the rescuers access to the hand holes.

In operation the victim is carefully placed on the top cover. One of the rescuers then restrains the victim at one end, typically by the ankles, while another rescuer slides the top cover off at the opposite end. As the top cover is removed, the victim descends onto the mattress, thus minimizing additional trauma to the victim arranging him on the mattress which is then evacuated to firmly support the victim for transportation to an aid facility.

Obviously many modifications and variations of the present invention are possible in light of the above teachings. It is therefore to be understood that within the scope of the appended claims the invention may be practiced otherwise than as specifically described.

What is claimed as new and desired to be secured by Letters Patent of the United States is:

1. An emergency spinal immobilization and extrication device comprising:

a gasproof flexible container, further comprising a plurality of flexible sub-containers in the shape of a human body, each sub-container filled with a plurality of deformable and resilient particles each sub-container containing perforations sufficiently small that the gas but not the particles, may travel freely from any sub-container to another, wherein the densities of particles in the sub-containers are approximately proportional to the weight of that portion of the human body resting upon the sub-container;

means attached to the container, for inflating and deflating the container with a gas;

a rigid baseplate beneath the container supporting the container, said baseplate containing hand-holes for lifting the device, side pieces attached to the base plate, and a top cover slideably mounted to the side pieces, enclosing the container therein, so that a trauma victim may be first placed on the inflated container by rescuers, and then the container deflated, thereby causing the victim to be securely supported by the particles as they cling together in the absence of the gas, and allowing the victim to be lifted and transported by the rescuers without causing additional trauma.

* * * * *